United States Patent
Krizman et al.

(10) Patent No.: US 9,840,728 B2
(45) Date of Patent: Dec. 12, 2017

(54) SRM ASSAY TO INDICATE CANCER THERAPY

(71) Applicant: Expression Pathology, Inc., Rockville, MD (US)

(72) Inventors: David B. Krizman, Gaithersburg, MD (US); Todd Hembrough, Gaithersburg, MD (US); Sheeno Thyparambil, Frederick, MD (US); Wei-Li Liao, Herndon, VA (US)

(73) Assignee: Expression Pathology, Inc., Rockville, MD (US)

(*) Notice: Subject to any disclaimer, the term of this patent is extended or adjusted under 35 U.S.C. 154(b) by 0 days.

(21) Appl. No.: 14/855,154

(22) Filed: Sep. 15, 2015

(65) Prior Publication Data
US 2015/0376678 A1 Dec. 31, 2015

Related U.S. Application Data

(63) Continuation of application No. PCT/US2014/031138, filed on Mar. 18, 2014.

(60) Provisional application No. 61/791,833, filed on Mar. 15, 2013.

(51) Int. Cl.
| | | |
|---|---|---|
| *A61K 38/10* | (2006.01) | |
| *A61K 38/00* | (2006.01) | |
| *C12Q 1/37* | (2006.01) | |
| *G01N 33/574* | (2006.01) | |
| *G01N 33/68* | (2006.01) | |
| *C07K 16/40* | (2006.01) | |
| *C12N 9/10* | (2006.01) | |
| *C12N 9/12* | (2006.01) | |

(52) U.S. Cl.
CPC ............... *C12Q 1/37* (2013.01); *C07K 16/40* (2013.01); *C12N 9/1007* (2013.01); *C12N 9/12* (2013.01); *G01N 33/57484* (2013.01); *G01N 33/6848* (2013.01); *C07K 2317/34* (2013.01); *C12Y 201/01045* (2013.01); *C12Y 207/10001* (2013.01); *G01N 2560/00* (2013.01); *G01N 2800/52* (2013.01); *G01N 2800/56* (2013.01); *G01N 2800/7028* (2013.01)

(58) Field of Classification Search
None
See application file for complete search history.

(56) References Cited

U.S. PATENT DOCUMENTS

| | | | |
|---|---|---|---|
| 7,473,532 | B2 | 1/2009 | Darfler et al. |
| 7,501,286 | B2 | 3/2009 | Gygi et al. |
| 7,632,686 | B2 | 12/2009 | Anderson |
| 2005/0064422 | A1 | 3/2005 | Barnidge et al. |
| 2009/0215636 | A1 | 8/2009 | Krizman et al. |
| 2011/0281289 | A1 | 11/2011 | Cutillas et al. |
| 2012/0208824 | A1 | 8/2012 | Rimkunas et al. |
| 2013/0011408 | A1 | 1/2013 | Krizman et al. |

FOREIGN PATENT DOCUMENTS

| | | |
|---|---|---|
| JP | 2012197258 A | 10/2012 |
| KR | 20100005180 A | 1/2010 |
| WO | 2006127860 A2 | 11/2006 |
| WO | 2008127248 A2 | 10/2008 |
| WO | 2011087865 A1 | 7/2011 |
| WO | 2012019132 A2 | 2/2012 |
| WO | 2012075318 A2 | 6/2012 |

OTHER PUBLICATIONS

Han et al. 2008. Curr. Opin Chem Biol. 12:483-490.*
Elsheikh et al. 2007. Breast Cancer Res. 9:R23.*
Kris et al. 2014. JAMA 311:1998-2006.*
McClaine et al. 2010. Neoplasia. 12:650.*
Mulligan 2014. Nature Reviews, Cancer. 14:173.*
Geng, M., et al.: "Proteomics of glycoproteins based on affinity selection of glycopeptides from tryptic digests." Journal of Chromatography B, 752:293-306 (2001).
International Search Report and Written Opinion in International Application No. PCT/US2014/031138, dated Sep. 5, 2014, 10 pages.

(Continued)

*Primary Examiner* — Shulamith H Shafer
(74) *Attorney, Agent, or Firm* — Edell, Shapiro & Finnan, LLC

(57) ABSTRACT

The current disclosure provides for specific peptides, and derived ionization characteristics of the peptides, from the ALK, Ros, Ron, Ret, TS, and/or FGFR1 proteins that are particularly advantageous for quantifying the ALK, Ros, Ron, Ret, TS, and/or FGFR1 proteins directly in biological samples that have been fixed in formalin by the methods of Selected Reaction Monitoring (SRM) mass spectrometry, or as Multiple Reaction Monitoring (MRM) mass spectrometry. Such biological samples are chemically preserved and fixed wherein the biological sample is selected from tissues and cells treated with formaldehyde containing agents/fixatives including formalin-fixed tissue/cells, formalin-fixed/paraffin embedded (FFPE) tissue/cells, FFPE tissue blocks and cells from those blocks, and tissue culture cells that have been formalin fixed and or paraffin embedded. A protein sample is prepared from the biological sample using the Liquid Tissue™ reagents and protocol and the ALK, Ros, Ron, Ret, TS, and/or FGFR1 proteins are quantitated in the Liquid Tissue™ sample by the method of SRM/MRM mass spectrometry, by quantitating in the protein sample at least one or more of the peptides described. These peptides can be quantitated if they reside in a modified or an unmodified form. An example of a modified form of an ALK, Ros, Ron, Ret, TS, and/or FGFR1 fragment peptide is phosphorylation of a tyrosine, threonine, serine, and/or other amino acid residues within the peptide sequence.

13 Claims, No Drawings

(56) References Cited

OTHER PUBLICATIONS

English language translation of Office Action in corresponding Korean Application No. 10-2015-7028737, dated May 26, 2017 (7 pages).

* cited by examiner

SEQUENCE LISTING

<160> NUMBER OF SEQ ID NOS: 39

<210> SEQ ID NO 1
<211> LENGTH: 13
<212> TYPE: PRT
<213> ORGANISM: Homo sapiens

<400> SEQUENCE: 1

Ser Leu Ala Val Asp Phe Val Val Pro Ser Leu Phe Arg
1               5                   10

<210> SEQ ID NO 2
<211> LENGTH: 9
<212> TYPE: PRT
<213> ORGANISM: Homo sapiens

<400> SEQUENCE: 2

Asp Ser Phe Pro Phe Leu Ser His Arg
1               5

<210> SEQ ID NO 3
<211> LENGTH: 11
<212> TYPE: PRT
<213> ORGANISM: Homo sapiens

<400> SEQUENCE: 3

Ser Leu Ser Ala Val Asp Phe Phe Ala Leu Lys
1               5                   10

<210> SEQ ID NO 4
<211> LENGTH: 14
<212> TYPE: PRT
<213> ORGANISM: Homo sapiens

<400> SEQUENCE: 4

Ser Asn Gln Glu Val Leu Glu Phe Val Thr Ser Gly Gly Arg
1               5                   10

<210> SEQ ID NO 5
<211> LENGTH: 15
<212> TYPE: PRT
<213> ORGANISM: Homo sapiens

<400> SEQUENCE: 5

Asp Pro Glu Gly Val Pro Pro Leu Leu Val Ser Gln Gln Ala Lys
1               5                   10                  15

<210> SEQ ID NO 6
<211> LENGTH: 9
<212> TYPE: PRT
<213> ORGANISM: Homo sapiens

<400> SEQUENCE: 6

Ile Gln Asp Gln Leu Gln Leu Phe Arg
1               5

<210> SEQ ID NO 7
<211> LENGTH: 8
<212> TYPE: PRT
<213> ORGANISM: Homo sapiens

<400> SEQUENCE: 7

Gly Glu Gly Leu Leu Pro Val Arg
1               5

<210> SEQ ID NO 8
<211> LENGTH: 11
<212> TYPE: PRT
<213> ORGANISM: Homo sapiens

<400> SEQUENCE: 8

Glu Gly Val Thr Val Leu Ile Asn Glu Asp Lys
1               5                   10

<210> SEQ ID NO 9
<211> LENGTH: 8
<212> TYPE: PRT
<213> ORGANISM: Homo sapiens

<400> SEQUENCE: 9

Ile Leu Gln Val Glu Leu Val Arg
1               5

<210> SEQ ID NO 10
<211> LENGTH: 9
<212> TYPE: PRT
<213> ORGANISM: Homo sapiens

<400> SEQUENCE: 10

Leu His Val Leu Gly Pro Asp Leu Lys
1               5

<210> SEQ ID NO 11
<211> LENGTH: 8
<212> TYPE: PRT
<213> ORGANISM: Homo sapiens

<400> SEQUENCE: 11

Val Asp Gly Thr Ser Val Leu Arg
1               5

<210> SEQ ID NO 12
<211> LENGTH: 11
<212> TYPE: PRT
<213> ORGANISM: Homo sapiens

<400> SEQUENCE: 12

Asp Leu Ile Ser Phe Gly Leu Gln Val Ala Arg
1               5                   10

<210> SEQ ID NO 13
<211> LENGTH: 11
<212> TYPE: PRT
<213> ORGANISM: Homo sapiens

<400> SEQUENCE: 13

Asp Leu Asp Ser Ala Leu Leu Ala Glu Val Lys
1               5                   10

<210> SEQ ID NO 14
<211> LENGTH: 9
<212> TYPE: PRT
<213> ORGANISM: Homo sapiens

<400> SEQUENCE: 14

Thr Leu Gly Glu Gly Glu Phe Gly Lys
1               5

<210> SEQ ID NO 15

```
<211> LENGTH: 8
<212> TYPE: PRT
<213> ORGANISM: Homo sapiens

<400> SEQUENCE: 15

Asn Ile Leu Val Ala Glu Gly Arg
1               5

<210> SEQ ID NO 16
<211> LENGTH: 10
<212> TYPE: PRT
<213> ORGANISM: Homo sapiens

<400> SEQUENCE: 16

Ala Leu Pro Ser Thr Trp Ile Glu Asn Lys
1               5                   10

<210> SEQ ID NO 17
<211> LENGTH: 8
<212> TYPE: PRT
<213> ORGANISM: Homo sapiens

<400> SEQUENCE: 17

Ile Ser Asp Phe Gly Leu Ser Arg
1               5

<210> SEQ ID NO 18
<211> LENGTH: 10
<212> TYPE: PRT
<213> ORGANISM: Homo sapiens

<400> SEQUENCE: 18

Asp Val Tyr Glu Glu Asp Ser Tyr Val Lys
1               5                   10

<210> SEQ ID NO 19
<211> LENGTH: 12
<212> TYPE: PRT
<213> ORGANISM: Homo sapiens

<400> SEQUENCE: 19

Val Gly Pro Gly Tyr Leu Gly Ser Gly Gly Ser Arg
1               5                   10

<210> SEQ ID NO 20
<211> LENGTH: 9
<212> TYPE: PRT
<213> ORGANISM: Homo sapiens

<400> SEQUENCE: 20

Ala Gly Tyr Thr Thr Val Ala Val Lys
1               5

<210> SEQ ID NO 21
<211> LENGTH: 10
<212> TYPE: PRT
<213> ORGANISM: Homo sapiens

<400> SEQUENCE: 21

Asp Leu Leu Ser Glu Phe Asn Val Leu Lys
1               5                   10

<210> SEQ ID NO 22
<211> LENGTH: 7
<212> TYPE: PRT
```

<213> ORGANISM: Homo sapiens

<400> SEQUENCE: 22

Ala Thr Ala Phe His Leu Lys
1               5

<210> SEQ ID NO 23
<211> LENGTH: 6
<212> TYPE: PRT
<213> ORGANISM: Homo sapiens

<400> SEQUENCE: 23

Asn Leu Val Leu Gly Lys
1               5

<210> SEQ ID NO 24
<211> LENGTH: 6
<212> TYPE: PRT
<213> ORGANISM: Homo sapiens

<400> SEQUENCE: 24

Ile Leu Glu Asp Pro Lys
1               5

<210> SEQ ID NO 25
<211> LENGTH: 10
<212> TYPE: PRT
<213> ORGANISM: Homo sapiens

<400> SEQUENCE: 25

Ala Asp Gly Thr Asn Thr Gly Phe Pro Arg
1               5                   10

<210> SEQ ID NO 26
<211> LENGTH: 9
<212> TYPE: PRT
<213> ORGANISM: Homo sapiens

<400> SEQUENCE: 26

Gln Val Asn His Pro His Val Ile Lys
1               5

<210> SEQ ID NO 27
<211> LENGTH: 6
<212> TYPE: PRT
<213> ORGANISM: Homo sapiens

<400> SEQUENCE: 27

Gly Ser Thr Asn Ala Lys
1               5

<210> SEQ ID NO 28
<211> LENGTH: 6
<212> TYPE: PRT
<213> ORGANISM: Homo sapiens

<400> SEQUENCE: 28

Val Ile Asp Thr Ile Lys
1               5

<210> SEQ ID NO 29
<211> LENGTH: 6
<212> TYPE: PRT
<213> ORGANISM: Homo sapiens

<400> SEQUENCE: 29

Thr Asn Pro Asp Asp Arg
1               5

<210> SEQ ID NO 30
<211> LENGTH: 7
<212> TYPE: PRT
<213> ORGANISM: Homo sapiens

<400> SEQUENCE: 30

His Phe Gly Ala Glu Tyr Arg
1               5

<210> SEQ ID NO 31
<211> LENGTH: 9
<212> TYPE: PRT
<213> ORGANISM: Homo sapiens

<400> SEQUENCE: 31

Asp Glu Phe Pro Leu Leu Thr Thr Lys
1               5

<210> SEQ ID NO 32
<211> LENGTH: 11
<212> TYPE: PRT
<213> ORGANISM: Homo sapiens

<400> SEQUENCE: 32

Asp Phe Leu Asp Ser Leu Gly Phe Ser Thr Arg
1               5                   10

<210> SEQ ID NO 33
<211> LENGTH: 11
<212> TYPE: PRT
<213> ORGANISM: Homo sapiens

<400> SEQUENCE: 33

Gly Val Leu Glu Glu Leu Leu Trp Phe Ile Lys
1               5                   10

<210> SEQ ID NO 34
<211> LENGTH: 14
<212> TYPE: PRT
<213> ORGANISM: Homo sapiens

<400> SEQUENCE: 34

Glu Glu Gly Asp Leu Gly Pro Val Tyr Gly Phe Gln Trp Arg
1               5                   10

<210> SEQ ID NO 35
<211> LENGTH: 16
<212> TYPE: PRT
<213> ORGANISM: Homo sapiens

<400> SEQUENCE: 35

Ala Glu Asp Phe Gln Ile Glu Gly Tyr Asn Pro His Pro Thr Ile Lys
1               5                   10                  15

<210> SEQ ID NO 36
<211> LENGTH: 10
<212> TYPE: PRT
<213> ORGANISM: Homo sapiens

<400> SEQUENCE: 36

```
Asp Asp Val Gln Ser Ile Asn Trp Leu Arg
1               5                   10

<210> SEQ ID NO 37
<211> LENGTH: 10
<212> TYPE: PRT
<213> ORGANISM: Homo sapiens

<400> SEQUENCE: 37

Asp Gly Val Gln Leu Ala Glu Ser Asn Arg
1               5                   10

<210> SEQ ID NO 38
<211> LENGTH: 8
<212> TYPE: PRT
<213> ORGANISM: Homo sapiens

<400> SEQUENCE: 38

Leu His Ala Val Pro Ala Ala Lys
1               5

<210> SEQ ID NO 39
<211> LENGTH: 11
<212> TYPE: PRT
<213> ORGANISM: Homo sapiens

<400> SEQUENCE: 39

His Pro Ala Gln Leu Ala Asn Gly Gly Leu Lys
1               5                   10
```

SRM ASSAY TO INDICATE CANCER THERAPY

This application is a continuation of International Application No. PCT/US14/31138, filed Mar. 18, 2014, which claims the benefit of U.S. Provisional Application No. 61/791,833, filed Mar. 15, 2013, each entitled "SRM Assay to Indicate Cancer Therapy." The contents of each of which are hereby incorporated by reference in their entireties. This application also contains a sequence listing submitted electronically via EFS-web, which serves as both the paper copy and the computer readable form (CRF) and consists of a file entitled "001152_8033_US01_SEQ_LISTING", which was created on Sep. 15, 2015, which is 6,258 bytes in size, and which is also incorporated by reference in its entirety.

INTRODUCTION

Lung cancer is the most prevalent cancer (>200,000 new US cases/year) and has a low five-year survival rate (~15%). Therapy for lung cancer is transitioning from use of a limited selection of therapies, consisting of radiation, folate metabolism, platinum-based drugs, and/or taxol-based drugs, to more targeted treatments that require histological characterization of the tumor and/or the presence or absence of key biomarker or therapeutic target proteins. A full 80% of all lung cancers are of the non-small cell lung cancer (NSCLC) type and this general type can be broken down into 4 different subtypes based on histological analysis: adenocarcinoma, squamous cell carcinoma, bronchioalveolar carcinoma, and Large-cell undifferentiated carcinoma. The remaining 20% of lung cancers are known as small cell lung cancer (SCLC). Recently-utilized targeted cancer therapies have shown exciting success in treating both NSCLC and SCLC patients. A targeted approach to cancer therapy is most advantageous when growth of the cancer is driven by a specific target protein, or proteins, and where the target protein, or proteins, that are driving the cancer are specifically attacked by therapeutic agents designed and manufactured to inhibit the target protein, or proteins, and hence inhibit growth of the cancer. Peptides and peptide sequences are provided for use in an SRM/MRM assay which can be used to quantitatively determine which protein targets are expressed, or over-expressed, directly in tumor tissue derived from lung cancer patients. This permits improved treatment decisions for targeted lung cancer therapy. Also provided is an SRM/MRM assay which can be used to quantitatively determine which protein targets are expressed, or over-expressed, directly in tumor tissue derived from patients with cancers other than lung cancer for improving targeted treatment decisions for any other cancer that is not lung cancer.

SUMMARY

Specific peptides derived from subsequences of the following proteins are provided, ALK, Ros, Ron, Ret, TS, and FGFR1. ALK is also known as ALK tyrosine kinase receptor and CD246 and is referred to herein as ALK. Ros is also known as c-Ros receptor tyrosine kinase and is referred to herein as Ros. Ron is also known as Macrophage-stimulating protein receptor, CD136, and p185-Ron, and is referred to herein as Ron. Ret is also known as Proto-oncogene tyrosine-protein kinase receptor Ret and Proto-oncogene c-Ret, and is referred to herein as Ret. TS is also known as thymidylate synthase, and is referred to herein as TS. FGFR1 is also known as fibroblast growth factor receptor 1 and CD331, and is referred to herein as FGFR1.

The peptide sequence and fragmentation/transition ions for each peptide derived from proteins are potentially useful in a mass spectrometry-based Selected Reaction Monitoring (SRM) assay(s), which can also be referred to as a Multiple Reaction Monitoring (MRM) assay(s), hereinafter referred to as SRM/MRM assay(s). The use of peptides for SRM/MRM analysis of ALK, Ros, Ron, Ret, TS, and FGFR1 proteins and isoforms of those proteins is described.

One or more, two or more, three or more, four or more, or five or six SRM/MRM assay(s) can be used to detect the presence and measure relative or absolute quantitative levels of one or more of the specific peptides from the ALK, Ros, Ron, Ret, TS, and/or FGFR1 proteins, and thereby provide a means of measuring the total amount of each of those proteins in a given protein preparation obtained from a biological sample by mass spectrometry. All, or a portion of all of the available peptides from those proteins can also be analyzed simultaneously in a single SRM/MRM assay or can be analyzed in any combination of individual SRM/MRM assays. Each of the peptides provides a potential means of measuring the total amount of each of the corresponding proteins in a given protein preparation obtained from a biological sample by mass spectrometry.

The SRM/MRM assay(s) described herein can measure these peptides directly in complex protein lysate samples prepared from cells procured from patient tissue samples, such as formalin fixed cancer patient tissue (e.g., biopsies). Methods of preparing protein samples from formalin fixed tissue are described in U.S. Pat. No. 7,473,532, the contents of which are hereby incorporated by reference in their entirety. The methods described in that patent may conveniently be carried out using Liquid Tissue reagents and protocol available from Expression Pathology Inc. (Rockville, Md.).

Formaldehyde/formalin fixation of tissues surgically removed from cancer patients is the accepted convention in pathology practice. As a result, formaldehyde/formalin fixed paraffin embedded tissue is the most widely available form of tissues from those patients. Formaldehyde/formalin fixation typically employs aqueous solutions of formaldehyde referred to as formalin. "100%" formalin consists of a saturated solution of formaldehyde (about 40% formaldehyde by volume or 37% by mass) in water, with a small amount of stabilizer, usually methanol, to limit oxidation and degree of polymerization. The most common way in which tissue is preserved is to soak whole tissue for extended periods of time (8 hours to 48 hours) in aqueous formaldehyde, commonly termed 10% neutral buffered formalin, followed by embedding the fixed whole tissue in paraffin wax for long term storage at room temperature. Thus molecular analytical methods to analyze formalin fixed cancer tissue will be the most accepted and heavily utilized methods for analysis of cancer patient tissue.

Results from the SRM/MRM assay(s) can be used to correlate accurate and precise quantitative levels of any or all of these proteins, in addition to accurate and precise quantitative levels of potential isoforms of these proteins, within specific tissue samples (e.g., cancer tissue sample) of a patient or subject from whom the tissue (biological sample) was collected and preserved. This not only provides diagnostic information about the cancer, but also permits a physician or other medical professional to determine appropriate therapy for the patient or subject. Such an assay that provides diagnostically and therapeutically important information about levels of protein expression in a diseased tissue or in another patient/subject sample is termed a companion diagnostic assay. For example, such an assay can be designed to diagnose the stage, degree, or histology of a cancer and determine a therapeutic agent that will be most effective in stopping the cancer cells from growing, leading to the determination to which therapeutic agent that a patient or subject will most likely respond.

More specifically, detection and/or quantitation of one or more, two or more, three or more, four or more, five or more of the ALK, Ros, Ron, Ret, TS, and/or FGFR1 proteins, in cancer cells from a patient is indicative of cancer growth, most notably lung cancer, and identify proteins that can be targeted by targeted treatment regimens.

DETAILED DESCRIPTION

The assays described herein quantify or measure relative or absolute levels of specific unmodified peptides from proteins including ALK, Ros, Ron, Ret, TS, and/or FGFR1 proteins and also can measure relative or absolute levels of specific modified peptides from those proteins. Examples of modifications include phosphorylated amino acid residues and glycosylated amino acid residues that are present on the peptides.

Relative quantitative levels of proteins and potential isoforms, can be determined by the SRM/MRM methodology, for example by comparing SRM/MRM signature peak areas (e.g., signature peak area or integrated fragment ion intensity). Relative levels of individual ALK, Ros, Ron, Ret, TS, and/or FGFR1 peptides can be determined in different samples (e.g., a control sample and a sample prepared from a patient's or subject's tissue). Alternatively, where each peptide has its own specific SRM/MRM signature peak, it is possible to compare multiple SRM/MRM signature peak areas for one or more of ALK, Ros, Ron, Ret, TS, and/or FGFR1 signature peptides. By comparing peak areas it is possible to determine the relative ALK, Ros, Ron, Ret, TS, and/or FGFR1 protein and potential protein isoform content in one biological sample or in one or more additional or different biological samples. In this way, the relative amount of a particular peptide, or peptides, from the those proteins, and therefore the relative amount of the ALK, Ros, Ron, Ret, TS, and/or FGFR1 proteins, and their potential isoforms, can be determined, across multiple (e.g., two, three, four, five, or more) biological samples under the same experimental conditions can be determined. In addition, relative quantitation can be determined for a given peptide, or peptides, from the ALK, Ros, Ron, Ret, TS, and/or FGFR1 protein within a single sample by comparing the signature peak area for that peptide by SRM/MRM methodology to the signature peak area for another and different peptide, or peptides, from a different protein, or proteins, within the same protein preparation from the biological sample.

Using such methodologies the amount of a particular peptide from the ALK, Ros, Ron, Ret, TS, and/or FGFR1 protein, and therefore the amount of each of the corresponding proteins and their potential isoforms can be determined relative one to another within the same sample or in different samples. Since relative quantitation of an individual peptide, or peptides, may be conducted relative to the amount of another peptide, or peptides, within or between samples, it is possible to determine the relative amounts of the peptides present (e.g., by determining the peak area relative one to another), regardless of the absolute weight to volume or weight to weight amounts of the proteins in the biological sample. Thus, the amounts of ALK, Ros, Ron, Ret, TS, and/or FGFR1 peptide in the protein preparation from the biological sample may be used to determine the amounts of those proteins in and among various samples. Relative quantitative data about individual signature peak areas between different samples are generally normalized to the amount of protein analyzed per sample (e.g., the total protein concentration of a sample and the volume analyzed are used to normalize samples). Relative quantitation can be performed across many peptides from multiple proteins and the ALK, Ros, Ron, Ret, TS, and/or FGFR1 protein(s) simultaneously in a single sample and/or across many samples to gain further insight into relative protein amounts, and/or one peptide/protein with respect to other peptides/proteins.

Absolute quantitative levels of the ALK, Ros, Ron, Ret, TS, and/or FGFR1 proteins are determined by, for example, the SRM/MRM methodology whereby the SRM/MRM signature peak area of an individual peptide from the ALK, Ros, Ron, Ret, TS, and/or FGFR1 proteins in one biological sample is compared to the SRM/MRM signature peak area of a known amount of one or more internal standards "spiked" in the sample in known amounts (e.g., isotope labeled standards). In one embodiment, the internal standard is a synthetic version of the same exact ALK, Ros, Ron, Ret, TS, and/or FGFR1 peptide that contains one or more amino acid residues labeled with one or more heavy isotopes. Such isotope labeled internal standards are synthesized so mass spectrometry analysis generates a predictable and consistent SRM/MRM signature peak that is different and distinct from the native ALK, Ros, Ron, Ret, TS, and/or FGFR1 peptide signature peak and which can be used as a comparator peak. Thus, when the internal standard is spiked in known amounts into a protein or peptide preparation from a biological sample in known amounts and analyzed by mass spectrometry, the SRM/MRM signature peak area of the native peptide can be compared to the SRM/MRM signature peak area of the internal standard peptide. The numerical comparison permits a calculation of either the absolute molarity and/or absolute weight of the native peptide present in the original protein preparation from the biological sample, from which the concentration or weight of the corresponding protein may be determined Absolute quantitative data for fragment peptides are typically displayed according to the amount of protein analyzed per sample. Absolute quantitation can be performed across many peptides, which permits a quantitative determination of multiple proteins (e.g., two, three, four, five, etc.) simultaneously in a single sample and/or across multiple samples to gain insight into absolute protein amounts in individual biological samples and/or in entire cohorts of individual samples. In one embodiment, the quantitation of proteins may be conducted using peptide standards as described by Gygi et al in U.S. Pat. No. 7,501,286.

Unless otherwise specified, as used herein the terms quantify, quantifying, measure or measuring mean to determine relative or absolute levels of an analyte, such as a protein, polypeptide, peptide, a standard (e.g., an internal standard).

Assay methods described herein can be used as an aid for determining the stage of the cancer when employing, for example, patient-derived or subject-derived tissue, such as formalin fixed tissue. The SRM/MRM assays described herein may also be used as an aid in determining which therapeutic agent would be most advantageous for use in treating that patient or subject.

To examine the levels of the proteins associated with lung cancer described herein, analysis can be conducted on cancerous tissue or tissue that is suspected of being cancerous that is removed from a patient or subject, either through surgical removal of partial or entire tumors, or through biopsy procedures conducted to determine the presence or absence of suspected disease. Samples of the tissues are analyzed to determine whether or not one or more of ALK, Ros, Ron, Ret, TS, and/or FGFR1 protein(s), and which forms of those proteins, are present in a patient's or subject's tissue. Moreover, the expression level of one or more of those proteins can be determined and compared to a "normal" or reference level found in healthy tissue. Normal or reference levels of proteins found in healthy tissue may be derived from, for example, the relevant tissues of one or more individuals that do not have cancer. Alternatively, normal or reference levels may be obtained for individuals with cancer by analysis of relevant tissues (e.g., portions of the same organ) not affected by the cancer.

Levels or amounts of proteins or peptides can be defined as the quantity expressed in moles, mass or weight of a protein or peptide determined by the SRM/MRM assay. The level or amount may be normalized to the total level or amount of protein or another component in the lysate analyzed (e.g., expressed in micromoles/microgram of protein or micrograms/microgram of protein) or even normalized to the amount of DNA on a per weight basis (e.g., micromoles or micrograms/microgram of DNA). In addition, the level or amount of a protein or peptide may be determined on a volume basis, expressed, for example, in micromolar or nanograms/microliter. The level or amount of protein or peptide as determined by the SRM/MRM assay can also be normalized to the number of cells analyzed.

Information regarding ALK, Ros, Ron, Ret, TS, and/or FGFR1 proteins, and isoforms of these proteins, can be used to aid in determining histological stage or grade of a cancer by correlating or comparing the level of the ALK, Ros, Ron, Ret, TS, and/or FGFR1 proteins, and their isoforms, or fragment peptides with the levels observed in normal tissues. Once the histological stage and/or grade, and/or ALK, Ros, Ron, Ret, TS, and/or FGFR1 protein-expression characteristics of the cancer has been determined, that information can be matched to a list of therapeutic agents (chemical and biological) developed to specifically treat cancer tissue that is characterized by, for example, abnormal expression of the protein or protein(s) (e.g., ALK, Ros, Ron, Ret, TS, and/or FGFR1) that were assayed. Matching information from an ALK, Ros, Ron, Ret, TS, and/or FGFR1 protein assay from a specific individual to a list of therapeutic agents that specifically targets cells/tissue expressing the ALK, Ros, Ron, Ret, TS, and/or FGFR1 protein(s) represents a personalized medicine approach to treating cancer including lung cancer. The assay methods described herein form the foundation of a personalized medicine approach by using analysis of proteins from the patient's or subject's own tissue as a source for diagnostic and treatment decisions.

Peptide Generation

In principle, any predicted peptide derived from the ALK, Ros, Ron, Ret, TS, and/or FGFR1 protein, prepared by any proteolytic process of known specificity may be used as a surrogate reporter to determine the abundance of ALK, Ros, Ron, Ret, TS, and/or FGFR1 proteins. In one embodiment samples are digested with a protease or proteases of known specificity (e.g. one or more of trypsin and/or Endoproteinase Lys-C). One or more peptides resulting from the proteolytic treatment can be used as a surrogate reporter to determine the abundance of one or more of ALK, Ros, Ron, Ret, TS, and/or FGFR1 proteins in a suitable assay such as a mass spectrometry-based SRM/MRM assay. Similarly, any predicted peptide sequence containing an amino acid residue at a site that is known to be modified in the ALK, Ros, Ron, Ret, TS, and/or FGFR1 proteins may also be used to assay the extent of modification of ALK, Ros, Ron, Ret, TS, and/or FGFR1 proteins in a sample.

ALK, Ros, Ron, Ret, TS, and/or FGFR1 fragment peptides may be generated by a variety of means including by the use of the Liquid Tissue™ protocol provided in U.S. Pat. No. 7,473,532. The Liquid Tissue™ protocol and reagents are capable of producing peptide samples suitable for mass spectroscopic analysis from formalin fixed paraffin embedded tissue by proteolytic digestion of the proteins in the tissue/biological sample. In the Liquid Tissue™ protocol the tissue/biological is maintained at elevated temperatures in a buffer for an extended period of time (e.g., from about 80° C. to about 100° C. for a period of time from about 10 minutes to about 4 hours) to reverse or release protein cross-linking. The buffer employed is a neutral buffer, (e.g., a Tris-based buffer, or a buffer containing a detergent) and advantageously is a buffer that does not interfere with mass spectrometric analysis. Next, the tissue/biological sample is treated with one or more proteases including, but not limited to, trypsin, chymotrypsin, pepsin, and Endoproteinase Lys-C for a time sufficient to disrupt the tissue and cellular structure of said biological sample and to liquefy said sample (e.g., a period of time from about 30 minutes to about 24 hours at a temperature from about 37° C. to about 65° C.). The result of the heating and proteolysis is a liquid, soluble, dilutable biomolecule lysate. In one embodiment two or more proteases selected from trypsin, chymotrypsin, pepsin, and Endoproteinase Lys-C are employed in the proteolytic treatment of the biological sample.

Peptide Separation and Assay

Once lysates are prepared, peptides in the samples may be subject to a variety of techniques that facilitate their analysis and measurement (quantification). Where analysis is conducted by mass spectrometry, one or more chromatographic methods may be employed in order to facilitate the analysis.

In one embodiment the peptides are separated by liquid chromatography (LC) prior to analysis by a mass spectrometer instrument. For example, peptides can be separated on a nanoAcquityLC system (Waters, Milford, Mass.) or EASY-nLC II (Thermo Scientific, San Jose, Calif.) with a PicoFrit (100 µm ID/10 µm tip ID, New Objective) column self-packed to a bed length of 12 cm with Jupiter Proteo 90Å C12, 4 µm resin (Phenomenex, Torrance, Calif.). Peptides can be eluted over a 12 min chromatography gradient from 1% to 50% acetonitrile, containing 0.1% formic acid and at a flow rate of 800 nL/min Once separated by liquid chromatography, the eluted peptides are directed into a mass spectrometer for analysis. In one embodiment, mass spectrometer is equipped with a nanospray source.

In another embodiment, the peptides may be separated by an affinity technique, such as for example immunologically-based purification (e.g., immunoaffinity chromatography), chromatography on ion selective media or, if the peptides are modified, by separation using appropriate media such as lectins for separation of carbohydrate modified peptides. In still another embodiment, the SISCAPA method, which employs immunological separation of peptides prior to mass spectrometric analysis, is employed. The SISCAPA technique is described, for example, in U.S. Pat. No. 7,632,686. In still other embodiments, lectin affinity methods (e.g., affinity purification and/or chromatography may be used to separate peptides from a lysate prior to analysis by mass spectrometry. Methods for separation of groups of peptides, including lectin-based methods, are described, for example, in Geng et al., J. Chromatography B, 752:293-306 (2001) Immunoaffinity chromatography techniques, lectin affinity techniques and other forms of affinity separation and/or chromatography (e.g., reverse phase, size based separation, ion exchange) may be used in any suitable combination to facilitate the analysis of peptides by mass spectrometry.

Surprisingly, it was found that many potential peptide sequences from the ALK, Ros, Ron, Ret, TS, and/or FGFR1 proteins are unsuitable or ineffective for use in mass spectrometry-based SRM/MRM assays for reasons that are not evident. In particular it was found that many tryptic peptides from the ALK, Ros, Ron, Ret, TS, and/or FGFR1 proteins could not be detected efficiently or at all in a Liquid Tissue™ lysate from formalin fixed, paraffin embedded tissue. As it was not possible to predict the most suitable peptides for MRM/SRM assay, it was necessary to experimentally identify modified and unmodified peptides in actual Liquid Tissue™ lysates to develop a reliable and accurate SRM/MRM assay for the ALK, Ros, Ron, Ret, TS, and/or FGFR1 proteins. While not wishing to be bound by any theory, it is believed that some peptides might, for example, be difficult to detect by mass spectrometry as they do not ionize well or produce fragments distinct from other proteins, peptides may also fail to resolve well in separation (e.g., liquid chromatography), or adhere to glass or plastic ware. Accordingly, those peptides from the ALK, Ros, Ron, Ret, TS, and/or FGFR1 proteins that can be detected in a Liquid Tissue™ lysate (e.g., the peptides in Tables 1 and 2) prepared from a formalin fixed tissue sample are the peptides for which SRM/MRM assays can be employed in an ALK, Ros, Ron, Ret, TS, and/or FGFR1 proteins SRM/MRM assay. In one embodiment the protease employed in the simultaneous preparation of fragments of the ALK, Ros, Ron, Ret, TS, and/or FGFR1 proteins in a single sample will be trypsin.

ALK, Ros, Ron, Ret, TS, and/or FGFR1 peptides found in various embodiments described herein (e.g., Tables 1 and/or 2) were derived from the ALK, Ros, Ron, Ret, TS, and/or FGFR1 proteins by trypsin digestion of all the proteins within a complex Liquid Tissue™ lysate prepared from cells procured from formalin fixed cancer tissue. Unless noted otherwise, in each instance the protease was trypsin. The Liquid Tissue™ lysate was then analyzed by mass spectrometry to determine those peptides derived from the ALK, Ros, Ron, Ret, TS, and/or FGFR1 proteins that are detected and analyzed by mass spectrometry. Identification of a specific preferred subset of peptides for mass spectrometric analysis is based on: 1) experimental determination of which peptide or peptides from a protein ionize in mass spectrometry analyses of Liquid Tissue™ lysates, and 2) the ability of the peptide to survive the protocol and experimental conditions used in preparing a Liquid Tissue™ lysate. This latter property extends not only to the amino acid sequence of the peptide but also to the ability of a modified amino acid residue within a peptide to survive in modified form during the sample preparation.

Protein lysates from cells procured directly from formalin (formaldehyde) fixed tissue were prepared using the Liquid Tissue™ reagents and protocol that entails collecting cells into a sample tube via tissue microdissection followed by heating the cells in the Liquid Tissue™ buffer for an extended period of time. Once the formalin-induced cross linking has been negatively affected, the tissue/cells are then digested to completion in a predictable manner using a protease, such as trypsin, although other proteases can be used. Each protein lysate is turned into a collection of peptides by digestion of intact polypeptides with the protease. Each Liquid Tissue™ lysate was analyzed (e.g., by ion trap mass spectrometry) to perform multiple global proteomic surveys of the peptides where the data was presented as identification of as many peptides as could be identified by mass spectrometry from all cellular proteins present in each protein lysate. An ion trap mass spectrometer or another form of a mass spectrometer that is capable of performing global profiling, for identification of as many peptides as possible from a single complex protein/peptide lysate is typically employed for analysis. Although SRM/MRM assay can be developed and performed on any type of mass spectrometer, including a MALDI, ion trap, or triple quadrupole, the most advantageous instrument platform for SRM/MRM assay is often considered to be a triple quadrupole instrument platform.

Once as many peptides as possible were identified in a single MS analysis of a single lysate under the conditions employed, then that list of peptides was collated and used to determine the proteins that were detected in that lysate. That process was repeated for multiple Liquid Tissue™ lysates, and the very large list of peptides was collated into a single dataset. That type of dataset can be considered to represent the peptides that can be detected in the type of biological sample that was analyzed (after protease digestion), and specifically in a Liquid Tissue™ lysate of the biological sample, and thus includes the peptides for specific proteins, such as for example the ALK, Ros, Ron, Ret, TS, and/or FGFR1 proteins.

In one embodiment, the ALK, Ros, Ron, Ret, TS, and/or FGFR1 tryptic peptides identified as useful in the determination of absolute or relative amounts of: ALK (e.g., NCBI Accession No.: Q9UM73, SEQ ID NO:1, SEQ ID NO:2, SEQ ID NO:3, SEQ ID NO:4, and SEQ ID NO:5), Ros (e.g., NCBI Accession No.: P08922, SEQ ID NO:6, SEQ ID NO:7, and SEQ ID NO:8; Ron (e.g., NCBI Accession No.: Q04912, SEQ ID NO: 9, SEQ ID NO:10, SEQ ID NO:11. SEQ ID NO:12, and SEQ ID NO:13); Ret (e.g., NCBI Accession No.: P07949, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26); TS (e.g., NCBI Accession No.: P04818, SEQ ID NO:27, SEQ ID NO:28, SEQ ID NO:29, SEQ ID NO:30, SEQ ID NO:31, SEQ ID NO:32, SEQ ID NO:33, SEQ ID NO:34, and SEQ ID NO:35), and/or FGFR1 (e.g., NCBI Accession No.: P11362, SEQ ID NO:36, SEQ ID NO:37, SEQ ID NO:38, and SEQ ID NO:39), include one or more, two or more, three or more, four or more, five or more, six or more, seven or more, eight or more, nine or more, or ten or more or all of the peptides of SEQ ID NO:1, SEQ ID NO:2, SEQ ID NO:3, SEQ ID NO:4, SEQ ID NO:5, SEQ ID NO:6, SEQ ID NO:7, SEQ ID NO:8 SEQ ID NO:9, SEQ ID NO:10, SEQ ID NO:11, SEQ ID NO:12, SEQ ID NO:13, SEQ ID NO:14, SEQ ID NO:15, SEQ ID NO:16. SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, and SEQ ID NO:39, each of which are listed in Table 1. Each of those peptides was detected by mass spectrometry in Liquid Tissue™ lysates prepared from formalin fixed, paraffin embedded tissue. Thus, each of the peptides in Table 1, or any combination of those peptides (e.g., one or more, two or more, three or more, four or more, five or more, six or more, seven or more, eight or more, nine or more, or ten or more of those peptides recited in Table 1) are candidates for use in quantitative SRM/MRM assay for the ALK, Ros, Ron, Ret, TS, and/or FGFR1 proteins including directly in formalin fixed patient or subject tissue.

TABLE 1

| SEQ ID | Protein | Peptide Sequence |
| --- | --- | --- |
| SEQ ID NO: 1 | ALK | SLAVDFVVPSLFR |
| SEQ ID NO: 2 | ALK | DSFPFLSHR |
| SEQ ID NO: 3 | ALK | SLSAVDFFALK |
| SEQ ID NO: 4 | ALK | SNQEVLEFVTSGGR |
| SEQ ID NO: 5 | ALK | DPEGVPPLLVSQQAK |
| SEQ ID NO: 6 | ROS | IQDQLQLFR |
| SEQ ID NO: 7 | ROS | GEGLLPVR |
| SEQ ID NO: 8 | ROS | EGVTVLINEDK |
| SEQ ID NO: 9 | RON | ILQVELVR |
| SEQ ID NO: 10 | RON | LHVLGPDLK |
| SEQ ID NO: 11 | RON | VDGTSVLR |
| SEQ ID NO: 12 | RON | DLISFGLQVAR |
| SEQ ID NO: 13 | RON | DLDSALLAEVK |
| SEQ ID NO: 14 | RET | TLGEGEFGK |
| SEQ ID NO: 15 | RET | NILVAEGR |
| SEQ ID NO: 16 | RET | ALPSTWIENK |
| SEQ ID NO: 17 | RET | ISDFGLSR |
| SEQ ID NO: 18 | RET | DVYEEDSYVK |
| SEQ ID NO: 19 | RET | VGPGYLGSGGSR |
| SEQ ID NO: 20 | RET | AGYTTVAVK |
| SEQ ID NO: 21 | RET | DLLSEFNVLK |
| SEQ ID NO: 22 | RET | ATAFHLK |
| SEQ ID NO: 23 | RET | NLVLGK |
| SEQ ID NO: 24 | RET | ILEDPK |
| SEQ ID NO: 25 | RET | ADGTNTGFPR |
| SEQ ID NO: 26 | RET | QVNHPHVIK |
| SEQ ID NO: 27 | TS | GSTNAK |
| SEQ ID NO: 28 | TS | VIDTIK |
| SEQ ID NO: 29 | TS | TNPDDR |
| SEQ ID NO: 30 | TS | HFGAEYR |
| SEQ ID NO: 31 | TS | DEFPLLTTK |
| SEQ ID NO: 32 | TS | DFLDSLGFSTR |
| SEQ ID NO: 33 | TS | GVLEELLWFIK |
| SEQ ID NO: 34 | TS | EEGDLGPVYGFQWR |
| SEQ ID NO: 35 | TS | AEDFQIEGYNPHPTIK |
| SEQ ID NO: 36 | FGFR1 | DDVQSINWLR |
| SEQ ID NO: 37 | FGFR1 | DGVQLAESNR |
| SEQ ID NO: 38 | FGFR1 | LHAVPAAK |
| SEQ ID NO: 39 | FGFR1 | HPAQLANGGLK |

The ALK, Ros, Ron, Ret, TS, and/or FGFR1 peptides listed in Table 1 include those detected from multiple Liquid Tissue™ lysates of multiple different formalin fixed tissues of different human organs including prostate, colon, and breast. Each of those peptides is considered useful for quantitative SRM/MRM assay of the ALK, Ros, Ron, Ret, TS, and/or FGFR1 proteins in formalin fixed tissue. Further data analysis of these experiments indicated no preference is observed for any specific peptides from any specific organ site. Thus, each of these peptides is believed to be suitable for conducting SRM/MRM assays of the ALK, Ros, Ron, Ret, TS, and/or FGFR1 proteins on a Liquid Tissue™ lysate from any formalin fixed tissue originating from any biological sample or from any organ site in the body.

In another embodiment, an SRM/MRM assay employs one or two peptides for each of TS and FGFR1 (e.g., from the peptides listed in Table 1). In another embodiment an SRM/MRM assay employs one or two peptides for each of ALK, Ros, Ron, and/or Ret (e.g., from the peptides listed in Table 1).

In other embodiments one or both of the ALK and Ros proteins are assayed and one, two three or four of the Ron, Ret, TS, and/or FGFR1 protein are assayed using SRM/MRM assay(s). In one example of such an embodiment, at least one peptide or at least two peptides for one or both of the Ron and Ret protein are assayed by SRM/MRM assay (e.g., the Ron and Ret peptides listed in Table 1); and at least one peptide or at least two peptides for any one, two, three or four of ALK, Ros, TS, and/or FM-RI are assayed (e.g., the peptides listed in Table 1). In another example of such an embodiment: at least one or at least two peptides for one or both of the ALK and Ros protein are assayed by SRM/MRM assay (e.g., peptides listed in Table 1); and at least one or at least two peptides for any of Ron, Ret, TS, and/or FGFR1 are assayed (e.g., the peptides listed in Table 1). Compositions comprising peptides that are isotopically labeled, but otherwise identical to one or more of the peptides set forth in any of these embodiments are provided for herein and their preparation and use, particularly for use as mass spectrometry standards, is described below.

In one embodiment one or more peptides in Table 1, or any combination of those peptides (e.g., one or more, two or more, three or more, four or more, five or more, six or more, seven or more, eight or more, nine or more, or all eleven) is assayed by a method that does not rely upon mass spectroscopy, including, but not limited to, immunological methods (e.g., Western blotting or ELISA). In one embodiment, the assays are conducted using formalin fixed tissue. Regardless of how information directed to the amount of the peptide(s) (absolute or relative) is obtained, the information may be employed in any of the methods described herein, including indicating (diagnosing) the presence of cancer in a patient or subject, determining the stage/grade/status of the cancer, providing a prognosis, or determining the therapeutic or treatment regimen for a patient or subject.

In other embodiments one or both of the ALK and Ros proteins are assayed and one, two three or four of the Ron, Ret, TS, and FGFR1 proteins are assayed by a method that does not rely upon mass spectroscopy, including, but not limited to, immunological methods (e.g., Western blotting or ELISA). In one example of such an embodiment: at least one or at least two peptides for one or both of the ALK and Ros proteins are assayed (e.g., the ALK and ROS peptides listed in Table 1); and at least one or at least two peptides for any one, two, three or four of Ron, Ret, TS, and FGFR1 proteins are assayed (e.g., the peptides listed in Table 1). In another example of such an embodiment: at least one or at least two peptides for one or both of the ALK and Ron proteins are (e.g., the ALK and Ron peptides listed in Table 1); and at least one or at least two peptides for any of Ros, Ret, TS, and FGFR1 proteins are assayed (e.g., the peptides listed in Table 1).

An important consideration when conducting an SRM/MRM assay is the type of instrument that may be employed in the analysis of the peptides. Although SRM/MRM assays can be developed and performed on any type of mass spectrometer, including a MALDI, ion trap, or triple quadrupole, presently the most advantageous instrument platform for SRM/MRM assay is often considered to be a triple quadrupole instrument platform. That type of a mass spectrometer may be considered to be the most suitable instrument for analyzing a single isolated target peptide within a very complex protein lysate that may consist of hundreds of thousands to millions of individual peptides from all the proteins contained within a cell.

In order to most efficiently implement a SRM/MRM assay for each peptide derived from the ALK, Ros, Ron, Ret, TS, and/or FGFR1 proteins it is desirable to utilize information in addition to the peptide sequence in the analysis. That additional information may be used in directing and instructing the mass spectrometer (e.g. a triple quadrupole mass spectrometer) to perform the correct and focused analysis of specific targeted peptide(s) such that the assay may be effectively performed.

The additional information about target peptides in general, and about specific ALK, Ros, Ron, Ret, TS, and/or FGFR1 peptides, may include one, two, three, four, or more of the mono isotopic mass of each peptide, its precursor charge state, the precursor m/z value, the m/z transition ions, and the ion type of each transition ion. Additional peptide information that may be used to develop an SRM/MRM assay for the ALK, Ros, Ron, Ret, TS, and/or FGFR1 proteins is shown in Table 2 for 12 ALK, Ros, Ron, Ret, TS, and/or FGFR1 peptides from the list in Table 1. This additional information described for the peptides as shown in Table 2 may be prepared, obtained, and applied to the analysis of any other peptides from the ALK, Ros, Ron, Ret, TS, and/or FGFR1 proteins, including those produced by the action of other proteases or combinations of proteases (e.g., trypsin and/or Lys C).

TABLE 2

| | Peptide Sequence | Mono isotopic mass | Precursor Charge State | Precursor m/z | Transition m/z | Ion Type |
|---|---|---|---|---|---|---|
| ALK SEQ ID | | | | | | |
| 1 | SLAVDFVVPSLFR | 1448.8027 | 2 | 725.409 | 619.356 | y5 |
| | | | 2 | 725.409 | 718.424 | y6 |
| | | | 2 | 725.409 | 817.493 | y7 |
| | | | 2 | 725.409 | 964.561 | y8 |
| | | | 2 | 725.409 | 1079.588 | Y9 |
| 2 | DSFPFLSHR | 1104.5352 | 2 | 553.275 | 512.293 | y4 |
| | | | 2 | 553.275 | 659.362 | y5 |
| | | | 2 | 553.275 | 756.415 | y6 |
| 4 | SNQEVLEFVTSGGR | 1521.7423 | 2 | 761.878 | 723.378 | y7 |
| | | | 2 | 761.878 | 852.421 | y8 |
| | | | 2 | 761.878 | 965.505 | y9 |
| | | | 2 | 761.878 | 1064.573 | y10 |
| Ros SEQ ID | | | | | | |
| 6 | IQDQLQLFR | 1159.6349 | 2 | 580.825 | 435.271 | y3 |
| | | | 2 | 580.825 | 563.33 | y4 |
| | | | 2 | 580.825 | 676.414 | y5 |
| | | | 2 | 580.825 | 804.472 | y6 |
| | | | 2 | 580.825 | 919.499 | y7 |
| 7 | GEGLLPVR | 839.4865 | 2 | 420.75 | 371.24 | y3 |
| | | | 2 | 420.75 | 484.324 | y4 |
| | | | 2 | 420.75 | 654.429 | y6 |
| Ron SEQ ID | | | | | | |
| 9 | ILQVELVR | 968.6018 | 2 | 485.308 | 516.314 | y4 |
| | | | 2 | 485.308 | 615.382 | y5 |
| | | | 2 | 485.308 | 743.441 | y6 |
| | | | 2 | 485.308 | 856.525 | y7 |
| 10 | LHVLGPDLK | 990.5862 | 2 | 496.3 | 529.298 | y5 |
| | | | 2 | 496.3 | 642.382 | y6 |
| | | | 2 | 496.3 | 741.45 | y7 |

TABLE 2-continued

| Peptide Sequence | Mono isotopic mass | Precursor Charge State | Precursor m/z | Transition m/z | Ion Type |
|---|---|---|---|---|---|
| Ret SEQ ID | | | | | |
| 16 ALPSTWIENK | 936.4552 | 2 | 579.811 | 390.198 | y3 |
| | | 2 | 579.811 | 503.282 | y4 |
| | | 2 | 579.811 | 689.361 | y5 |
| | | 2 | 579.811 | 790.409 | y6 |
| | | 2 | 579.811 | 877.441 | y7 |
| TS SEQ ID | | | | | |
| 31 DEFPLLTTK | 1062.5597 | 2 | 532.287 | 462.292 | y4 |
| | | 2 | 532.287 | 575.376 | y5 |
| | | 2 | 532.287 | 672.429 | y6 |
| | | 2 | 532.287 | 819.497 | y7 |
| 35 AEDFQIEGYNPHPTI | 1857.8897 | 3 | 620.304 | 458.297 | y4 |
| | | 3 | 620.304 | 578.293 | y10 |
| | | 3 | 620.304 | 634.835 | y11 |
| | | 3 | 620.304 | 692.408 | y6 |
| | | 3 | 620.304 | 829.912 | y14 |
| FGFR1 SEQ ID | | | | | |
| 36 DDVQSINWLR | 1244.6149 | 2 | 623.315 | 588.325 | y4 |
| | | 2 | 623.315 | 701.409 | y5 |
| | | 2 | 623.315 | 788.441 | y6 |
| | | 2 | 623.315 | 916.499 | y7 |
| 38 LHAVPAAK | 805.481 | 2 | 403.748 | 386.239 | y4 |
| | | 2 | 403.748 | 485.308 | y5 |
| | | 2 | 403.748 | 556.345 | y6 |

In some embodiments, the peptides suitable for assays of ALK, Ros, Ron, Ret, TS, and/or FGFR1 proteins (e.g., the peptides set forth in Table 1 and shown as SEQ ID, Nos. 1-39) may contain additional proteolytic sites internal to the peptide sequences that if cleaved would produce sub-peptides. Such sub-peptides are recognizable by assessing the sequence of the identified peptides for proteolytic cleavage sites of a desired protease. In one embodiment, tryptic peptides may include additional internal trypsin cleavage sites that can lead to sub-peptides upon further cleavage by trypsin. In another embodiment, tryptic peptides may contain internal sites for proteases including, but not limited to, trypsin GluC, AspN, chymotrypsin, and/or Lys C, which can lead to the formation of sub-peptides upon cleavage by any one, two, or more of trypsin, GluC, AspN, chymotrypsin, and/or Lys C. In another embodiment, Lys C peptides may contain internal sites for other proteases, such as GluC, AspN, chymotrypsin, and/or trypsin, which can lead to the formation of sub-peptides upon cleavage by any one, two, or more of GluC, AspN, chymotrypsin, and/or trypsin. Such sub-peptides, and specifically trypsin, GluC, AspN, chymotrypsin, and/or Lys C cleavage fragments of any one or more of the peptides set forth in SEQ ID Nos. 1-39 are understood to be set forth and within the scope of this disclosure.

Embodiments set forth herein include compositions comprising one or more of the peptides in Tables 1 and 2, and may optionally include peptides that are isotopically labeled but otherwise identical to one or more of the peptides found in Tables 1 and 2. In some embodiments, the compositions comprise one or more, two or more, three or more, four or more, five or more, six or more, seven or more, eight or more, nine or more, or all thirty-nine (39) of the peptides in Tables 1 and 2. Such compositions may optionally include peptides, polypeptides, or proteins whose amino acid sequence comprises peptides that are isotopically labeled but otherwise identical to one or more of the peptides found in Table 1 and Table 2. Where isotopically labeled synthetic or natural peptides, polypeptides, or proteins that comprise one, two, three, four, five, six or more of the peptides in Tables 1 and 2 are employed, protease treatment releases peptides that are isotopically labeled but otherwise identical to the peptides in Tables 1 and 2. Such isotopically labeled biological or biosynthetic peptides may be prepared, for example, in programmed cell lysates or in tissue culture using isotopically labeled amino acids. Each of the isotopically labeled peptides may be labeled with one or more isotopes selected independently from the group consisting of: $^{18}O$, $^{17}O$, $^{34}S$, $^{15}N$, $^{13}C$, $^{2}H$ or combinations thereof. Compositions comprising peptides from the ALK, Ros, Ron, Ret, TS, and/or FGFR1 proteins, whether isotope labeled or not, do not need to contain all of the peptides from that protein (e.g., a complete set of tryptic peptides). In some embodiments the compositions do not contain all peptides in combination from ALK, Ros, Ron, Ret, TS, and/or FGFR1 proteins, and particularly all of the peptides appearing in Table 1 and Table 2. Compositions containing peptides may be in the form of dried or lyophilized materials, liquid (e.g., aqueous) solutions or suspensions, arrays, or blots.

In one embodiment, the additional information about specific ALK, Ros, Ron, Ret, TS, and/or FGFR1 peptides includes one or more, two or more, or three or more of the mono isotopic mass of each peptide, its precursor charge state, the precursor m/z value, the m/z transition ions, and the ion type of each transition ion for peptides resulting from Lys C proteolysis of ALK, Ros, Ron, Ret, TS, and/or FGFR1 proteins.

In another embodiment, the additional information about specific ALK, Ros, Ron, Ret, TS, and/or FGFR1 peptides, includes one or more, two or more, or three or more of the mono isotopic mass of each peptide, its precursor charge state, the precursor m/z value, the m/z transition ions, and the ion type of each transition ion for peptides resulting from trypsin proteolysis of ALK, Ros, Ron, Ret, TS, and/or FGFR1 proteins.

In still another embodiment, the additional information about specific ALK, Ros, Ron, Ret, TS, and/or FGFR1 peptides, includes one or more, two or more, or three or more of the mono isotopic mass of each peptide, its precursor charge state, the precursor m/z value, the m/z transition ions, and the ion type of each transition ion for peptides resulting from trypsin and/or Lys C proteolysis of ALK, Ros, Ron, Ret, TS, and/or FGFR1 proteins. In one embodiment, a single tryptic and/or Lys C proteolytic peptide from each of the ALK, Ros, Ron, Ret, TS, and/or FGFR1 proteins, along with the relevant additional information is employed in a diagnostic determination. Thus, for example, the peptides of SEQ ID NOs 4, 7, 9, 16, 31 and/or 36, and additional information about those peptides (see Table 3) in employed in a diagnostic analysis.

TABLE 3

|   | Peptide sequence | Mono Isotopic Mass | Precursor Charge State | Precursor m/z | Transition m/z | Ion Type |
|---|---|---|---|---|---|---|
| ALK SEQ ID | | | | | | |
| SEQ ID NO: 4 | SNQEVLEFVTSGGR | 1521.742 | 2 | 761.878 | 723.378 | y7 |
| | | | 2 | 761.878 | 852.421 | y8 |
| | | | 2 | 761.878 | 965.505 | y9 |
| | | | 2 | 761.878 | 1064.573 | y10 |
| Ros SEQ ID | | | | | | |
| SEQ ID NO: 7 | GEGLLPVR | 839.4865 | 2 | 420.75 | 371.24 | y3 |
| | | | 2 | 420.75 | 484.324 | y4 |
| | | | 2 | 420.75 | 654.429 | y6 |
| Ron SEQ ID | | | | | | |
| SEQ ID NO: 9 | ILQVELVR | 968.6018 | 2 | 485.308 | 516.314 | y4 |
| | | | 2 | 485.308 | 615.382 | y5 |
| | | | 2 | 485.308 | 743.441 | y6 |
| | | | 2 | 485.308 | 856.525 | y7 |
| Ret SEQ ID | | | | | | |
| SEQ ID NO: 16 | ALPSTWIENK | 936.4552 | 2 | 579.811 | 390.198 | y3 |
| | | | 2 | 579.811 | 503.282 | y4 |
| | | | 2 | 579.811 | 689.361 | y5 |
| | | | 2 | 579.811 | 790.409 | y6 |
| | | | 2 | 579.811 | 877.441 | y7 |
| TS SEQ ID | | | | | | |
| SEQ ID NO: 31 | DEFPLLTTK | 1062.56 | 2 | 532.287 | 462.292 | y4 |
| | | | 2 | 532.287 | 575.376 | Y5 |
| | | | 2 | 532.287 | 672.429 | y6 |
| | | | 2 | 532.287 | 819.497 | y7 |
| FGFR1 SEQ ID | | | | | | |
| SEQ ID NO: 36 | DDVQSINWLR | 1244.615 | 2 | 623.315 | 588.325 | y4 |
| | | | 2 | 623.315 | 701.409 | y5 |
| | | | 2 | 623.315 | 788.441 | y6 |
| | | | 2 | 623.315 | 916.499 | y7 |

CERTAIN EMBODIMENTS

Certain Embodiments of the Invention are Described Below.

1. A method for measuring the level of the ALK, Ros, Ron, Ret, TS, and/or FGFR1 proteins in a biological sample, comprising detecting and/or quantifying the amount of one or more modified and/or unmodified ALK, Ros, Ron, Ret, TS, and/or FGFR1 protein fragment peptides in a protein digest prepared from said biological sample using mass spectrometry; and calculating the level of modified or unmodified ALK, Ros, Ron, Ret, TS, and/or FGFR1 protein in said sample; and wherein said amount is a relative amount or an absolute amount.

2. The method of embodiment 1, further comprising the step of fractionating said protein digest prior to detecting and/or quantifying the amount of one or more modified or unmodified ALK, Ros, Ron, Ret, TS, and/or FGFR1 protein fragment peptides.

3. The method of embodiment 2, wherein said fractionating step is selected from the group consisting of gel electrophoresis, liquid chromatography, capillary electrophoresis, nano-reversed phase liquid chromatography, high performance liquid chromatography, or reverse phase high performance liquid chromatography.

4. The method of any of embodiments 1-3, wherein said protein digest of said biological sample is prepared by the Liquid Tissue™ protocol.

5. The method of any of embodiments 1-3, wherein said protein digest comprises a protease digest.

6. The method of embodiment 5, wherein said protein digest comprises a trypsin and/or lys C digest.

7. The method of any of embodiments 1-6, wherein said mass spectrometry comprises tandem mass spectrometry, ion trap mass spectrometry, triple quadrupole mass spectrometry, MALDI-TOF mass spectrometry, MALDI mass spectrometry, and/or time of flight mass spectrometry.

8. The method of embodiment 7, wherein the mode of mass spectrometry used is Selected Reaction Monitoring (SRM), Multiple Reaction Monitoring (MRM), and/or multiple Selected Reaction Monitoring (mSRM), or any combination thereof.

9. The method of any of embodiments 1 to 8, wherein the ALK, Ros, Ron, Ret, TS, and/or FGFR1 protein fragment peptides comprises an amino acid sequence as set forth as SEQ ID NO:1, SEQ ID NO:2, SEQ ID NO:3, SEQ ID NO:4, SEQ ID NO:5, SEQ ID NO:6, SEQ ID NO:7, SEQ ID NO:8 SEQ ID NO:9, SEQ ID NO:10, SEQ ID NO:11, SEQ ID NO:12, SEQ ID NO:13, SEQ ID NO:14, SEQ ID NO:15, SEQ ID NO:16. SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, and SEQ ID NO:39.

10. The method of any of embodiments 1-9, wherein the biological sample is a blood sample, a urine sample, a serum sample, an ascites sample, a sputum sample, lymphatic fluid, a saliva sample, a cell, or a solid tissue.

11. The method of any of embodiments 1-10, wherein the biological sample is formalin fixed tissue.

12. The method of any of embodiments 1-11, wherein the biological sample is paraffin embedded tissue.

13. The method of any of embodiments 1-12, wherein the biological sample is tissue that is obtained from a tumor.

14. The method of embodiment 13, wherein the tumor is a primary tumor.

15. The method of embodiment 13, wherein the tumor is a secondary tumor.

16. The method of any of embodiments 1 to 15, further comprising quantifying modified and/or unmodified ALK, Ros, Ron, Ret, TS, and/or FGFR1 protein fragment peptides.

17(a). The method of any of embodiments 1-16, wherein quantifying the ALK, Ros, Ron, Ret, TS, and/or FGFR1 protein fragment peptides comprises comparing an amount of one or more ALK, Ros, Ron, Ret, TS, and/or FGFR1 protein fragment peptides comprising an amino acid sequence of about 8 to about 45 amino acid residues of ALK, Ros, Ron, Ret, TS, and/or FGFR1 proteins in one biological sample to the amount of the same ALK, Ros, Ron, Ret, TS, and/or FGFR1 protein fragment peptides in a different and separate sample or biological sample.

17(b). The method of any of embodiments 1-16, wherein quantifying the ALK, Ros, Ron, Ret, TS, and/or FGFR1 protein fragment peptides comprises comparing an amount of one or more ALK, Ros, Ron, Ret, TS, and/or FGFR1 protein fragment peptides comprising an amino acid sequence of about 8 to about 45 amino acid residues of ALK, Ros, Ron, Ret, TS, and/or FGFR1 proteins, as shown in SEQ ID NO:1, SEQ ID NO:2, SEQ ID NO:3, SEQ ID NO:4, SEQ ID NO:5, SEQ ID NO:6, SEQ ID NO:7, SEQ ID NO:8 SEQ ID NO:9, SEQ ID NO:10, SEQ ID NO:11, SEQ ID NO:12, SEQ ID NO:13, SEQ ID NO:14, SEQ ID NO:15, SEQ ID NO:16. SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, and SEQ ID NO:39, in one biological sample to the amount of the same ALK, Ros, Ron, Ret, TS, and/or FGFR1 protein fragment peptides in a different and separate biological sample.

18. The method of embodiment 17(a) or 17(b), wherein quantifying one or more ALK, Ros, Ron, Ret, TS, and/or FGFR1 protein fragment peptides comprises determining the amount of each of the ALK, Ros, Ron, Ret, TS, and/or FGFR1 protein fragment peptides in a biological sample by comparison to an added internal standard peptide of known amount, wherein each of the ALK, Ros, Ron, Ret, TS, and/or FGFR1 protein fragment peptides in the biological sample is compared to an added internal standard peptide having the same amino acid sequence.

19. The method of embodiment 18, wherein the internal standard peptide is an isotopically labeled peptide.

20. The method of embodiment 19, wherein the isotopically labeled internal standard peptide comprises one or more heavy stable isotopes selected from $^{18}O$, $^{17}O$, $^{34}S$, $^{15}N$, $^{13}C$, $^{2}H$ or combinations thereof.

21. The method of any of embodiments 1-20, wherein detecting and/or quantifying the amount of one or more modified or unmodified ALK, Ros, Ron, Ret, TS, and/or FGFR1 protein fragment peptides in the protein digest indicates the presence of modified and/or unmodified ALK, Ros, Ron, Ret, TS, and/or FGFR1 protein and an association with cancer in a patient or subject.

22. The method of embodiment 21, further comprising correlating the results of said detecting and/or quantifying the amount of one or more modified and/or unmodified ALK, Ros, Ron, Ret, TS, and/or FGFR1 protein fragment peptides, or the amount of said ALK, Ros, Ron, Ret, TS, and/or FGFR1 proteins to the diagnostic stage/grade/status of the cancer.

23. The method of embodiment 22, wherein correlating the results of said detecting and/or quantifying the amount of one or more modified or unmodified ALK, Ros, Ron, Ret, TS, and/or FGFR1 protein fragment peptides, or the amount of said ALK, Ros, Ron, Ret, TS, and/or FGFR1 proteins to the diagnostic stage/grade/status of the cancer is combined with detecting and/or quantifying the amount of other proteins or peptides from other proteins in a multiplex format to provide additional information about the diagnostic stage/grade/status of the cancer.

24. The method of any one of embodiments 1-23, further comprising selecting for a patient or subject from which said biological sample was obtained a treatment based on the presence, absence, or amount of one or more ALK, Ros, Ron, Ret, TS, and/or FGFR1 protein fragment peptides or the amount of ALK, Ros, Ron, Ret, TS, and/or FGFR1 proteins.

25. The method of any one of embodiments 1-24, further comprising administering to a patient or subject from which said biological sample was obtained a therapeutically effective amount of a therapeutic agent, wherein the therapeutic agent and/or amount of the therapeutic agent administered is based upon amount of one or more modified or unmodified ALK, Ros, Ron, Ret, TS, and/or FGFR1 protein fragment peptides or the amount of ALK, Ros, Ron, Ret, TS, and/or FGFR1 proteins.

26. The method of embodiments 24 and 25, wherein the treatment or the therapeutic agent is directed to cancer cells expressing ALK, Ros, Ron, Ret, TS, and/or FGFR1 proteins.

27. The method of embodiments 1-27, wherein the biological sample is formalin fixed tumor tissue that has been processed for quantifying the amount of one or more modified or unmodified ALK, Ros, Ron, Ret, TS, and/or FGFR1 protein fragment peptides employing the Liquid Tissue™ protocol and reagents.

28. The method of any of embodiments 1-28, wherein said one or more modified or unmodified ALK, Ros, Ron, Ret, TS, and/or FGFR1 protein fragment peptides is one or more of the peptides in Table 1.

29. A composition comprising one or more, two or more, three or more, four or more, five or more, six or more, seven or more, eight or more, nine or more, or ten or more of the peptides in Table 1 and/or antibodies thereto.

30. The composition of embodiment 30, comprising one or more, two or more, three or more, four or more, five or more, six or more, seven or more, eight or more, nine or more, or ten or more of the peptides of Table 2 or antibodies thereto.

Exemplary SRM/MRM Assay Method

1. The method described below was used to: 1) identify candidate peptides from the ALK, Ros, Ron, Ret, TS, and/or FGFR1 proteins that can be used for a mass spectrometry-based SRM/MRM assay for the ALK, Ros, Ron, Ret, TS, and/or FGFR1 proteins, 2) develop individual SRM/MRM assay, or assays, for target peptides from the ALK, Ros, Ron, Ret, TS, and/or FGFR1 proteins, and 3) apply quantitative assays to cancer diagnosis and/or choice of optimal therapy. Identification of SRM/MRM candidate fragment peptides for the ALK, Ros, Ron, Ret, TS, and/or FGFR1 proteins:
    a. Prepare a Liquid Tissue™ protein lysate from a formalin fixed biological sample using a protease or proteases, (that may or may not include trypsin), to digest proteins
    b. Analyze all protein fragments in the Liquid Tissue™ lysate on an ion trap tandem mass spectrometer and identify all fragment peptides from the ALK, Ros, Ron, Ret, TS, and/or FGFR1 proteins, where individual fragment peptides do not contain any peptide modifications such as phosphorylations or glycosylations
    c. Analyze all protein fragments in the Liquid Tissue™ lysate on an ion trap tandem mass spectrometer and identify all fragment peptides from the ALK, Ros, Ron, Ret, TS, and/or FGFR1 proteins that carry peptide modifications such as for example phosphorylated or glycosylated residues
    d. All peptides generated by a specific digestion method from the entire, full length ALK, Ros, Ron, Ret, TS, and/or FGFR1 proteins potentially can be measured, but preferred peptides used for development of the SRM/MRM assay are those that are identified by mass spectrometry directly in a complex Liquid Tissue™ protein lysate prepared from a formalin fixed biological sample
    e. Peptides that are specifically modified (phosphorylated, glycosylated, etc.) in a patient or subject tissue and which ionize, and thus can be detected, in a mass spectrometer when analyzing a Liquid Tissue™ lysate from a formalin fixed biological sample are identified as candidate peptides for assaying peptide modifications of the ALK, Ros, Ron, Ret, TS, and/or FGFR1 proteins 2. Mass Spectrometry Assay for Fragment Peptides from ALK, Ros, Ron, Ret, TS, and/or FGFR1 proteins:
    a. SRM/MRM assay on a triple quadrupole mass spectrometer for individual fragment peptides identified in a Liquid Tissue™ lysate is applied to peptides from the ALK, Ros, Ron, Ret, TS, and/or FGFR1 proteins
        i. Determine optimal retention time for a fragment peptide for optimal chromatography conditions including but not limited to gel electrophoresis, liquid chromatography, capillary electrophoresis, nano-reversed phase liquid chromatography, high performance liquid chromatography, or reverse phase high performance liquid chromatography
        ii. Determine the mono isotopic mass of the peptide, the precursor charge state for each peptide, the precursor m/z value for each peptide, the m/z transition ions for each peptide, and the ion type of each transition ion for each fragment peptide in order to develop an SRM/MRM assay for each peptide.
        iii. An SRM/MRM assay can then be conducted using the information from (i) and (ii) on a triple quadrupole mass spectrometer where each peptide has a characteristic and unique SRM/MRM signature peak that precisely defines the unique SRM/MRM assay as performed on a triple quadrupole mass spectrometer
    b. Perform SRM/MRM analysis so that the amount of the fragment peptide of the ALK, Ros, Ron, Ret, TS, and/or FGFR1 proteins that is detected, as a function of the unique SRM/MRM signature peak area from an SRM/MRM mass spectrometry analysis, can indicate both the relative and absolute amount of the ALK, Ros, Ron, Ret, TS, and/or FGFR1 proteins in a particular protein lysate.
        i. Relative quantitation may be achieved by:
            1. Determining increased or decreased presence of the ALK, Ros, Ron, Ret, TS, and/or FGFR1 proteins by comparing (a) the SRM/MRM signature peak area from a given ALK, Ros, Ron, Ret, TS, and/or FGFR1 peptide detected in a Liquid Tissue™ lysate from one formalin fixed biological sample to (b) the same SRM/MRM signature peak area of the same ALK, Ros, Ron, Ret, TS, and/or FGFR1 fragment peptide in at least a second, third, fourth or more Liquid Tissue™ lysates from at least a second, third, fourth or more formalin fixed biological samples
            2. Determining increased or decreased presence of the ALK, Ros, Ron, Ret, TS, and/or FGFR1 proteins by comparing (a) the SRM/MRM signature peak area from a given ALK, Ros, Ron, Ret, TS, and/or FGFR1 peptide detected in a Liquid Tissue™ lysate from one formalin fixed biological sample to (b) SRM/MRM signature peak areas developed from fragment peptides from other proteins, in other samples derived from different and separate biological sources, where the SRM/MRM signature peak area comparison between the 2 samples for a peptide fragment is normalized to amount of protein analyzed in each sample.
3. Determining increased or decreased presence of the ALK, Ros, Ron, Ret, TS, and/or FGFR1 proteins by (a) comparing the SRM/MRM signature peak area for a given ALK, Ros, Ron, Ret, TS, and/or FGFR1 peptide to (b) the SRM/MRM signature peak areas from other fragment peptides derived from different proteins within the same Liquid Tissue™ lysate from the formalin fixed biological sample in order to normalize changing levels of ALK, Ros, Ron, Ret, TS, and/or FGFR1 proteins to levels of other proteins that do not change their levels of expression under various cellular conditions.
4. These assays can be applied to both unmodified fragment peptides and to modified fragment peptides of the ALK, Ros, Ron, Ret, TS, and/or FGFR1 proteins, where the modifications include but are not limited to phosphorylation and/or glycosylation, and where the relative levels of modified peptides are determined in the same manner as determining relative amounts of unmodified peptides.

ii. Absolute quantitation of a given peptide may be achieved by comparing (a) the SRM/MRM signature peak area for a given fragment peptide from the ALK, Ros, Ron, Ret, TS, and/or FGFR1 proteins in an individual biological sample to (b) the SRM/MRM signature peak area of an internal fragment peptide standard spiked into the protein lysate from the biological sample
1. The internal standard is a labeled synthetic version of the fragment peptide from the ALK, Ros, Ron, Ret, TS, and/or FGFR1 proteins that is being interrogated. This standard is spiked into a sample in known amounts, and the SRM/MRM signature peak area can be determined for both the internal fragment peptide standard and the native fragment peptide in the biological sample separately, followed by comparison of both peak areas
2. This can be applied to unmodified fragment peptides and modified fragment peptides, where the modifications include but are not limited to phosphorylation and/or glycosylation, and where the absolute levels of modified peptides can be determined in the same manner as determining absolute levels of unmodified peptides.

3. Apply Fragment Peptide Quantitation to Cancer Diagnosis and Treatment
a. Perform relative and/or absolute quantitation of fragment peptide levels of the ALK, Ros, Ron, Ret, TS, and/or FGFR1 proteins and demonstrate that the previously-determined association, as well understood in the field of cancer, of ALK, Ros, Ron, Ret, TS, and/or FGFR1 protein expression to the stage/grade/status of cancer in patient or subject tumor tissue is confirmed
b. Perform relative and/or absolute quantitation of fragment peptide levels of the ALK, Ros, Ron, Ret, TS, and/or FGFR1 proteins and demonstrate correlation with clinical outcomes from different treatment strategies, wherein this correlation has already been demonstrated in the field or can be demonstrated in the future through correlation studies across cohorts of patients or subjects and tissue from those patients or subjects.

Once either previously established correlations or correlations derived in the future are confirmed by this assay then the assay method can be used to determine optimal treatment strategy A Mass Spectrometry Assay for Fragment Peptides from ALK, Ros, Ron, Ret, TS, and/or FGFR1 Proteins
a. SRM/MRM assay to determine the amount of the fragment peptide of the ALK, Ros, Ron, Ret, TS, and/or FGFR1 proteins that is detected to determine the relative and/or absolute amount of the ALK, Ros, Ron, Ret, TS, and/or FGFR1 proteins in a protein lysate.
i. Relative quantitation may be achieved by:
1. Determining increased or decreased presence of the ALK, Ros, Ron, Ret, TS, and/or FGFR1 proteins by comparing (a) the SRM/MRM signature peak area from a given ALK, Ros, Ron, Ret, TS, and/or FGFR1 protein peptide detected in a Liquid Tissue™ lysate from one formalin fixed biological sample to (b) the same SRM/MRM signature peak area of the same ALK, Ros, Ron, Ret, TS, and/or FGFR1 protein fragment peptide in at least a second, third, fourth or more Liquid Tissue™ lysates from at least a second, third, fourth or more formalin fixed biological samples
2. Determining increased or decreased presence of the ALK, Ros, Ron, Ret, TS, and/or FGFR1 proteins by comparing (a) the SRM/MRM signature peak area from a given ALK, Ros, Ron, Ret, TS, and/or FGFR1 protein peptide detected in a Liquid Tissue™ lysate from one formalin fixed biological sample to (b) SRM/MRM signature peak areas developed from fragment peptides from other proteins, in other samples derived from different and separate biological sources, where the SRM/MRM signature peak area comparison between the 2 samples for a peptide fragment is normalized to amount of protein analyzed in each sample.
3. Determining increased or decreased presence of the ALK, Ros, Ron, Ret, TS, and/or FGFR1 proteins by comparing (a) the SRM/MRM signature peak area for a given ALK, Ros, Ron, Ret, TS, and/or FGFR1 protein peptide to (b) the SRM/MRM signature peak areas from other fragment peptides derived from different proteins within the same Liquid Tissue™ lysate from the formalin fixed biological sample in order to normalize changing levels of ALK, Ros, Ron, Ret, TS, and/or FGFR1 proteins to levels of other proteins that do not change their levels of expression under various cellular conditions.
4. These assays can be applied to both unmodified fragment peptides and for modified fragment peptides of the ALK, Ros, Ron, Ret, TS, and/or FGFR1 proteins, where the modifications include but are not limited to phosphorylation and/or glycosylation, and where the relative levels of modified peptides are determined in the same manner as determining relative amounts of unmodified peptides.
ii. Absolute quantitation of a given peptide or the protein from which it is derived, may be achieved by comparing (a) the SRM/MRM signature peak area for a given fragment peptide from the ALK, Ros, Ron, Ret, TS, and/or FGFR1 proteins in an individual biological sample to (b) the SRM/MRM signature peak area of an internal fragment peptide standard spiked into the protein lysate from the biological sample.

The internal standard can be a labeled synthetic version of the fragment peptide from the ALK, Ros, Ron, Ret, TS, and/or FGFR1 proteins that is being interrogated (or a protein or polypeptide comprising the labeled synthetic version of the fragment peptide that is released upon proteolysis). The standard is spiked into a sample in known amounts, and the SRM/MRM signature peak area can be determined for both the internal fragment peptide standard and the native fragment peptide in the biological sample separately, followed by comparison of both peak areas.

This can be applied to unmodified fragment peptides and modified fragment peptides, where the modifications include but are not limited to phosphorylation and/or glycosylation, and where the absolute levels of modified peptides can be determined in the same manner as determining absolute levels of unmodified peptides.

Assessment of ALK, Ros, Ron, Ret, TS, and/or FGFR1 protein levels in tissues based on analysis of formalin fixed patient-derived or subject-derived tissue can provide diagnostic, prognostic, and therapeutically-relevant information about each particular patient or subject. Described herein is a method for measuring the levels of the ALK, Ros, Ron, Ret, TS, and/or FGFR1 proteins in a biological sample, comprising detecting and/or quantifying the amount of one or more modified or unmodified ALK, Ros, Ron, Ret, TS, and/or FGFR1 protein fragment peptides in a protein digest prepared from said biological sample using mass spectrometry; and calculating the level of modified or unmodified ALK, Ros, Ron, Ret, TS, and/or FGFR1 proteins in said sample; and wherein said level is a relative level or an absolute level. In a related embodiment, quantifying one or more ALK, Ros, Ron, Ret, TS, and/or FGFR1 protein fragment peptides comprises determining the amount of each of the ALK, Ros, Ron, Ret, TS, and/or FGFR1 protein fragment peptides in a biological sample by comparison to an added internal standard peptide of known amount, wherein each of the ALK, Ros, Ron, Ret, TS, and/or FGFR1 protein fragment peptides in the biological sample is compared to an internal standard peptide having the same amino acid sequence. In some embodiments the internal standard is an isotopically labeled internal standard peptide comprises one or more heavy stable isotopes selected from $^{18}O$, $^{17}O$, $^{34}S$, $^{15}N$, $^{13}C$, $^{2}H$ or combinations thereof.

The method for measuring levels of the ALK, Ros, Ron, Ret, TS, and/or FGFR1 proteins in a biological sample described herein (or fragment peptides as surrogates thereof) may be used as a diagnostic indicator of cancer in a patient or subject. In one embodiment, the results from measurements of levels of the ALK, Ros, Ron, Ret, TS, and/or FGFR1 proteins may be employed to determine the diagnostic stage/grade/status of a cancer by correlating (e.g., comparing) the levels of ALK, Ros, Ron, Ret, TS, and/or FGFR1 proteins found in a tissue with the levels of ALK, Ros, Ron, Ret, TS, and/or FGFR1 proteins found in normal and/or cancerous or precancerous tissues.

The only current method in use for detecting levels of specific proteins in formalin fixed patient tissue is immunohistochemistry (IHC). This method analyzes only one protein at a time on a single tissue section from a patient tumor tissue sample. Thus, in order to analyze multiple proteins, multiple tissue sections must be interrogated, which costs much time and labor. IHC uses an antibody to detect the presence of the target protein and, because of the potential for non-specific binding of the antibody to proteins there is great inherent potential for signal background in any IHC experiment. In addition, IHC is only semi-quantitative at best. Due to these problems IHC fails to provide for objective quantitative analysis of multiple proteins simultaneously. The methods described here are able to provide for objective quantitation of the ALK, Ros, Ron, Ret, TS, and/or FGFR1 proteins simultaneously with 100% assay specificity utilizing a single section of a patient tissue sample, saving significant time and money while providing for much more valuable data about expression of the ALK, Ros, Ron, Ret, TS, and/or FGFR1 proteins.

This multiplex SRM/MRM assay can also include simultaneous analysis of other additional proteins beyond the ALK, Ros, Ron, Ret, TS, and/or FGFR1 proteins, including drug target proteins such as EGFR, IGF-1R, and cMet. This is valuable because analysis of additional proteins also indicates which additional drugs might be useful for treating a particular cancer. Examples of additional drugs based on analysis of additional example drug target proteins include Erbitux, which targets the EGFR receptor, Figitumumab, which targets IGF-1R, and Foretinib, which targets c-Met and vascular endothelial growth factor receptor 2 (VEGFR-2).

Because both nucleic acids and protein can be analyzed from the same Liquid Tissue™ biomolecular preparation, it is possible to generate additional information about disease diagnosis and drug treatment decisions from the nucleic acids in the same sample used for protein analysis. For example, if the ALK, Ros, Ron, Ret, TS, and/or FGFR1 proteins are expressed by certain cells at increased levels, when assayed by SRM the data can provide information about the state of the cells and their potential for uncontrolled growth, potential drug resistance and the development of cancers can be obtained. At the same time, information about the status of the ALK, Ros, Ron, Ret, TS, and/or FGFR1 genes and/or the nucleic acids and proteins they encode (e.g., mRNA molecules and their expression levels or splice variations) can be obtained from nucleic acids present in the same biomolecular preparation. In one embodiment, information about the ALK, Ros, Ron, Ret, TS, and/or FGFR1 proteins and/or one, two, three, four or more additional proteins may be assessed by examining the nucleic acids encoding those proteins. Those nucleic acids can be examined, for example, by one or more, two or more, or three or more of: sequencing methods, polymerase chain reaction methods, restriction fragment polymorphism analysis, identification of deletions, insertions, and/or determinations of the presence of mutations, including but not limited to, single base pair polymorphisms, transitions, transversions, or combinations thereof.

The above description and exemplary embodiments of methods and compositions are illustrative of the scope of the present disclosure. Because of variations which will be apparent to those skilled in the art, however, the present disclosure is not intended to be limited to the particular embodiments described above.

The invention claimed is:

1. A method for measuring the level of the human ALK protein in a human biological sample of formalin-fixed tissue, comprising detecting and quantifying using mass spectrometry the amount of an ALK protein fragment peptide in a protein digest prepared from said human biological sample; and calculating the level of ALK protein in said sample;
wherein said fragment peptide is the peptide of SEQ ID NO:5, and
wherein said amount is a relative amount or an absolute amount.

2. The method of claim 1, further comprising the step of fractionating said protein digest prior to detecting and quantifying the amount of said ALK protein fragment peptides.

3. The method of claim 1, wherein said protein digest comprises a protease digest.

4. The method of claim 1, wherein quantifying said ALK protein fragment peptide comprises comparing the amount of said ALK protein fragment peptide in one biological sample to the amount of the same ALK protein fragment peptide in a different and separate biological sample.

5. The method of claim 4, wherein quantifying said ALK protein fragment peptide comprises determining the amount said ALK protein fragment peptide in a biological sample by comparison to an added internal standard peptide of known amount, wherein the ALK protein fragment peptide in the biological sample is compared to an internal standard peptide having the same amino acid sequence.

6. The method of claim 5, wherein the internal standard peptide is an isotopically labeled peptide.

7. The method of claim 1, wherein detecting and quantifying the amount of said ALK protein fragment peptide in the protein digest indicates the presence of ALK protein and an association with cancer in a patient or subject.

8. The method of claim 7, further comprising correlating the results of said detecting and quantifying the amount of said ALK protein fragment peptide, or the amount of said ALK protein to the diagnostic stage/grade/status of the cancer.

9. The method of claim 8, wherein correlating the results of said detecting quantifying the amount of said ALK protein fragment peptide, or the amount of said ALK protein to the diagnostic stage/grade/status of the cancer is combined with detecting and/or quantifying the amount of other proteins or peptides from other proteins in a multiplex format to provide additional information about the diagnostic stage/grade/status of the cancer, including lung cancer.

10. The method of claim 8, further comprising administering to a patient or subject from which said biological sample was obtained a therapeutically effective amount of a therapeutic agent, wherein the therapeutic agent and/or amount of the therapeutic agent administered is based upon the amount of said ALK protein fragment or the amount of ALK protein.

11. The method of claim 10, wherein the treatment or the therapeutic agent is directed to cancer cells expressing ALK protein.

12. The method of claim 7, wherein said cancer is lung cancer.

13. The method of claim 1, further comprising detecting and quantifying the amount of a Ros protein fragment peptide in said protein digest.

* * * * *